United States Patent
Brunn et al.

(10) Patent No.: US 10,792,237 B2
(45) Date of Patent: Oct. 6, 2020

(54) AQUEOUS SURFACTANT COMPOSITIONS

(71) Applicant: BASF SE, Ludwigshafen (DE)

(72) Inventors: Claudia Brunn, Duesseldorf (DE); Ansgar Behler, Bottrop (DE); Detlev Stanislowski, Mettmann (DE); Monika Barbenheim, Bottrop (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/115,706

(22) PCT Filed: Jan. 23, 2015

(86) PCT No.: PCT/EP2015/051338
§ 371 (c)(1),
(2) Date: Aug. 1, 2016

(87) PCT Pub. No.: WO2015/117842
PCT Pub. Date: Aug. 13, 2015

(65) Prior Publication Data
US 2017/0007520 A1    Jan. 12, 2017

(30) Foreign Application Priority Data
Feb. 4, 2014   (EP) .................................... 14153835

(51) Int. Cl.
| | |
|---|---|
| *A61Q 19/10* | (2006.01) |
| *A61Q 5/02* | (2006.01) |
| *A61Q 19/00* | (2006.01) |
| *A61Q 5/00* | (2006.01) |
| *A61K 8/00* | (2006.01) |
| *A61K 8/72* | (2006.01) |
| *A61K 8/44* | (2006.01) |
| *A61K 8/46* | (2006.01) |
| *A61Q 9/02* | (2006.01) |
| *A61Q 11/00* | (2006.01) |
| *C11D 1/28* | (2006.01) |
| *C11D 1/90* | (2006.01) |
| *C11D 1/94* | (2006.01) |
| *C11D 17/00* | (2006.01) |

(52) U.S. Cl.
CPC .............. *A61K 8/466* (2013.01); *A61K 8/442* (2013.01); *A61Q 5/02* (2013.01); *A61Q 9/02* (2013.01); *A61Q 11/00* (2013.01); *A61Q 19/10* (2013.01); *C11D 1/28* (2013.01); *C11D 1/90* (2013.01); *C11D 1/94* (2013.01); *C11D 17/003* (2013.01); *A61K 2800/596* (2013.01)

(58) Field of Classification Search
CPC .......... A61Q 5/02; A61Q 19/10; A61Q 19/00; A61K 2800/596; A61K 8/442; A61K 8/466
See application file for complete search history.

(56) References Cited

U.S. PATENT DOCUMENTS

| | | | |
|---|---|---|---|
| 3,377,289 A | 4/1968 | Stein et al. | |
| 3,377,290 A | 4/1968 | Stein et al. | |
| 3,390,096 A | 6/1968 | Stein et al. | |
| 5,733,854 A * | 3/1998 | Chowdhary | A61K 8/20 424/70.13 |
| 6,172,026 B1 * | 1/2001 | Ospinal | C11D 1/37 510/152 |
| 2005/0153853 A1 * | 7/2005 | Sajic | C11D 3/046 510/141 |
| 2009/0200511 A1 * | 8/2009 | Allen | A61K 8/37 252/182.12 |
| 2009/0227482 A1 * | 9/2009 | Dong | A61K 8/466 510/125 |
| 2012/0208898 A1 | 8/2012 | Dong et al. | |
| 2014/0076344 A1 * | 3/2014 | Doi | A61K 8/361 132/202 |

FOREIGN PATENT DOCUMENTS

| | | |
|---|---|---|
| DE | 1216470 B | 5/1966 |
| DE | 1218646 B | 6/1966 |

(Continued)

OTHER PUBLICATIONS

International Search Report for International Patent Application No. PCT/EP2015/051338, dated May 26, 2015.

(Continued)

*Primary Examiner* — Tracy Liu
(74) *Attorney, Agent, or Firm* — Marshall, Gerstein & Borun LLP

(57) ABSTRACT

An aqueous surfactant composition comprising one or more alpha-sulfo fatty acid disalts (A) of the general formula (I), $$R^1CH(SO_3M^1)COOM^2 \quad (I),$$

wherein the radical $R^1$ is a linear or branched alkyl or alkenyl radical with 6 to 18 carbon atoms and the radicals $M^1$ and $M^2$, independently of one another, are selected from the group H, Li, Na, K, Ca/2, Mg/2, ammonium, and alkanolamine,
one or more amidoalkylbetaines (B) of the general formula (II), $$R^2-CO-NH-(CH_2)_y-N^+(CH_3)_2-CH_2-COO^- \quad (II)$$

in which the radical $R^2$ is a linear or branched alkyl or alkenyl radical with 7 to 19 carbon atoms and the index y is an integer in the range 2 to 4,
and water, where specific limiting conditions are to be observed.

The compositions are transparent, storage-stable, characterized by good foaming ability and good viscosity, and are suitable for cosmetic products and also detergents and cleaners.

17 Claims, No Drawings

(56) References Cited

FOREIGN PATENT DOCUMENTS

| | | |
|---|---|---|
| DE | 1221391 B | 7/1966 |
| DE | 1225799 B | 9/1966 |
| DE | 10 2007 038 029 A1 | 2/2009 |
| EP | 2 277 860 A1 | 1/2011 |
| WO | WO-92/15660 A1 | 9/1992 |
| WO | WO-2011/049932 A1 | 4/2011 |
| WO | WO-2011049932 A1 * | 4/2011 ............... A61K 8/20 |
| WO | WO-2014037167 A1 * | 3/2014 ............... C11D 9/02 |
| WO | WO-2015047260 A1 * | 4/2015 ............. C11D 3/221 |

OTHER PUBLICATIONS

Anonymous: "Foaming Hand Wash", GNDP (Global New Products Database), Jun. 1, 2006 (Jun. 1, 2006), Internet, pp. 1-2, Retrieved from the Internet <URL:http://www.gnpd.com/sinatra/recordpage/536439/from_search/YiRfThoNgE/with_sort/2/> [retrieved on Jul. 4, 2014].

Schambil, F., et al., "Physico-Chemical Properties of α-Sulpho Fatty Acid Methyl Esters and α-Sulpho Fatty Acid Di-Salts," *Tenside, Surfactants, Detergents* (1990), vol. 27, No. 6, pp. 380-385.

\* cited by examiner

AQUEOUS SURFACTANT COMPOSITIONS

CROSS-REFERENCE TO RELATED APPLICATIONS

This is the U.S. national phase of International Patent Application No. PCT/EP2015/051338, filed Jan. 23, 2015, which claims the benefit of European Patent Application No. 14153835.5, filed Feb. 4, 2014.

FIELD OF THE INVENTION

The present invention relates to aqueous surfactant compositions with a content of alpha-sulfo fatty acid disalts and specific amidoalkylbetaines.

PRIOR ART

Anionic surfactants are some of the most widespread interface-active compounds and, apart from being used in detergents and cleaners, are also used for diverse purposes in the field of cosmetics. Customary anionic surfactants as are used in particular in cosmetics are the salts of alkyl ether sulfates (alkyl polyether sulfates, fatty alcohol polyglycol ether sulfates, in short also ether sulfates). They are characterized by a strong foaming ability, high cleaning power, low sensitivity to hardness and grease and are used widely for producing cosmetic products such as, for example, hair shampoos, foam or shower baths, but also in hand dishwashing detergents.

For many current applications, apart from a good interface-active effect, further requirements are placed on anionic surfactants. A high dermatological compatibility is required in particular in cosmetics. Furthermore, an adequate solubility in water, good compatibility with as many as possible of the active ingredients and auxiliaries used in cosmetics, a good foaming ability and good thickenability are generally desired. Furthermore, there is a need for anionic surfactants which can be produced at least partially from biogenic sources and specifically also renewable raw materials. Furthermore, there is also a need for surfactants which have no alkoxylated groups and which thus render superfluous in particular the use of ethylene oxide for their production.

The so-called alpha-sulfo fatty acid disalts ("disalts") are a known class of surfactant but have a very poor solubility in water (cf. e.g. F. Schambil and M. J. Schwuger, Tenside Surf. Det. 27 (1990), 6, pp. 380-385): Thus, for example the solubility in water of C14-di-Na salt at 20° C. is only 0.7% (compare the graph on p. 381). This is unsatisfactorily low for practice, for example cosmetic preparations.

The fact that disalts are generally suitable as viscosity reducers for different anionic surfactant formulations has been known for a long time, compare e.g. DE-A-1216470, DE-A-1221391, DE-A-1218646 and DE-A-1,225799. All of these cases involve the use of disalt as hydrotrope, i.e. as substance with liquefying, viscosity-reducing properties. Accordingly, the person skilled in the art searching for viscosity-increasing substances would not consider the disalts disclosed therein on account of the teaching of these documents.

WO-A-92/15660 discloses liquid cleaners with a content of sulfo-oleic acid disalts. It is disclosed that sulfo-oleic acid disalts are able to reduce the viscosity of surfactants or surfactant mixtures for cleaners—particularly those based on fatty alkyl sulfates, fatty alkyl ether sulfates, alkylpolyglucosides and fatty acid monoethanolamides—and indeed just as effectively or even better than by adding ethanol or hydrotropes (page 2, second paragraph). In this connection, reference is made to the fact that sulfo-oleic acid disalts are very readily water-soluble, in total contrast to the alpha-sulfostearic acid disalt, which is sparingly water-soluble (compare the paragraph bridging pages 2 and 3). Finally, on page 3, lines 3-6, it is stated that $C_{12-14}$-disalts based on saturated fatty acids are viscosity-lowering. Accordingly, the person skilled in the art searching for viscosity-increasing substances would not take disalts into consideration on account of the teaching of this document.

WO-A-2011/049932 describes liquid cleaning compositions with a content of disalts and betaines. In this connection, it is essential to the invention that the betaines are alkylbetaines. The use of amidoalkylbetaines and in particular alkylamidopropylbetaines is expressly advised against. For example, on p. 9, lines 1 to 4, it expressly states that formulations with alkylbetaines or alkylsultaines have better properties than corresponding formulations with cocamidopropylbetaine. This is also explicitly demonstrated experimentally: Table 1 (page 28) reveals in the columns with the comparative experiments ("control 1" and "control 2") that the experiment to use cocamidopropylbetaine for thickening anionic surfactants, inter alia disalt, fails: extremely poor viscosity values were attained (<100 mPas or 200 mPas). Accordingly, the person skilled in the art searching for viscosity-increasing substances for aqueous formulations with a content of anionic surfactants, including disalts, would not take amidoalkylbetaines into consideration on account of the teaching of this document.

DESCRIPTION OF THE INVENTION

The complex object of the present invention was to provide aqueous surfactant compositions which are characterized by the properties specified below, with each of these properties constituting a technical feature:

Good transparency, which for the purposes of the present invention is to be understood as meaning that the aqueous surfactant compositions upon quantitative determination by means of a TurbiScan MA 2000 (measuring instrument from Formulaction) at 23° C. have an average transmission of at least 80%, preferably of at least 85% and in particular of at least 88%.

Adequately high viscosity, which for the purposes of the present invention is to be understood as meaning a value of 1000 mPas or higher (measured using a Brookfield RV laboratory rheometer at 23° C., 12 rpm, spindle set RV 02 to 07 (spindle choice depending on viscosity range)). As is known, "mPas" means millipascal seconds.

Shelf life at room temperature (23° C.) over at least 8 weeks without any visible changes (for example clouding, discoloration, phase separation, loss of transparency and the like) arising.

Good foaming ability. In this regard, it may be noted that in the field of cosmetics, foaming ability can be understood from different aspects, it being possible to use in particular foam volume, foam stability, foam elasticity, water content of the foam, optical features of the foam, for example, the pore size, and also the foam sensorics for the purposes of assessing the foam. It is particularly desirable for a surface-active formulation to have a large foam volume during initial foaming. In practice, the initial foaming takes place within a relatively short period (from a few seconds to one minute). Typically, during initial foaming, a shower gel or a shampoo is spread and caused to foam by rubbing between hands, skin and/or hair. An excellent foaming behavior is of fundamental importance in the context of the present invention for a good foaming ability. In the laboratory, the foaming behavior of an aqueous surfactant solution can be assessed e.g. by agitating the solution within a comparatively short time period by means of stirring, shaking, pumping, bubbling through a gas stream or in another way. The foam test used for the purposes of the present invention is described in more detail in the experimental section.

Hydrolysis stability in the acidic pH range, particularly at pHs of 5.8 or less).

The invention firstly provides aqueous surfactant compositions comprising one or more alpha-sulfo fatty acid disalts (A) of the general formula (I),

$$R^1CH(SO_3M^1)COOM^2 \quad (I),$$

in which the radical $R^1$ is a linear or branched alkyl or alkenyl radical with 6 to 18 carbon atoms and the radicals $M^1$ and $M^2$—independently of one another—are selected from the group H, Li, Na, K, Ca/2, Mg/2, ammonium and alkanolamine, one or more amidoalkylbetaines (B) of the general formula (II),

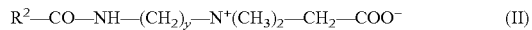

$$R^2-CO-NH-(CH_2)_y-N^+(CH_3)_2-CH_2-COO^- \quad (II)$$

in which the radical $R^2$ is a linear or branched alkyl or alkenyl radical with 7 to 19 carbon atoms and the index y is an integer in the range 2 to 4, water, where the following provisos apply:

with regard to compounds (A) it is the case that the fraction of the compounds (A) in which the radical $R^1$ is an alkenyl radical—based on the total amount of the compounds (A) in the aqueous surfactant compositions—is 3% by weight or less;

with regard to the compounds (B), it is the case that the fraction of the compounds (B) in which the radical $R^2$ is an alkenyl radical—based on the total amount of the compounds (B) in the aqueous surfactant compositions—is 3% by weight or less;

the content of the compounds (A) and (B) in the aqueous surfactant compositions is—based on the total aqueous surfactant composition—at least 5% by weight;

if the aqueous surfactant compositions comprises one or more ester sulfonates (E) of the general formula (V),

$$R^5CH(SO_3M^5)COOR^6 \quad (V)$$

in which the radical $R^5$ is a linear or branched alkyl or alkenyl radical with 6 to 18 carbon atoms and the radical $R^6$ is a linear or branched alkyl or alkenyl radical with 1 to 20 carbon atoms, where the radical $R^6$ can logically be an alkenyl radical or be branched only above 3 carbon atoms, and the radical $M^5$ is selected from the group Li, Na, K, Ca/2, Mg/2, ammonium and alkanolamines, it is the case that the compounds (A)—based on the totality of the compounds (A) and (E)—must be present to 50% by weight or more—and in particular to 90% by weight or more;

the weight ratio of the compounds (A):(B) in the aqueous surfactant compositions is in the range from 1:1.5 to 1:5;

the pH of the aqueous surfactant compositions is 5.8 or less;

the viscosity of the aqueous surfactant compositions—measured using a Brookfield RV laboratory rheometer at 23° C., 12 rpm, spindle set RV 02 to 07 (spindle choice depending on viscosity range)—is 1000 mPas or higher;

the average transmission of the aqueous surfactant compositions at 23° C.—measured using a TurbiScan MA 2000—is at least 80%.

For the sake of clarity, it may be established that the aqueous surfactant composition which is used for determining the average transmission must satisfy all of the aforementioned parameters.

Surprisingly, the aforementioned complex object was achieved in an excellent manner by the surfactant compositions according to the invention. In so doing, prejudices known from the prior art were overcome. It was also unforeseeable and at times highly surprising that disalts can be used in combination with amidoalkylbetaines in considerably higher concentrations, evident from the fact that the aqueous compositions are transparent and not cloudy. What is likewise surprising—especially also in view of the prior art cited above which teaches the use of disalt for lowering viscosity, and also the prior art, likewise cited above, which expressly advises against the use of cocamidopropylbetaine—is the occurrence of high viscosities when using a combination of disalts and amidoalkylbetaines.

The Compounds (A)

The compounds (A), which are referred to within the context of the present invention as alpha-sulfo fatty acid disalts, are obligatory for the aqueous surfactant compositions according to the invention. They have the aforementioned formula (I)

$$R^1CH(SO_3M^1)COOM^2 \quad (I),$$

in which the radical $R^1$ is a linear or branched alkyl or alkenyl radical with 6 to 18 carbon atoms and the radicals $M^1$ and $M^2$—independently of one another—are selected from the group H, Li, Na, K, Ca/2, Mg/2, ammonium and alkanolamines. Also applicable—as likewise stated above—is the proviso that the fraction of the compounds (A) in the aqueous surfactant compositions in which the radical $R^1$ is an alkenyl radical—based on the total amount of the compounds (A)—is 3% by weight or less.

In a preferred embodiment, the radical $R^1$ in the formula (I) means a saturated, linear radical with 10 to 16 carbon atoms, where, with regard to the compounds (A), it is the case that the fraction of the compounds (A) in which the radical $R^1$ is a decyl and/or a dodecyl radical—based on the total amount of the compounds (A)—is 90% by weight or more.

Preferably, the radicals $M^1$ and $M^2$ in the formula (I) are Na.

The compounds (A) can be prepared by all methods known appropriately to the person skilled in the art. A particularly preferred method of preparation here is the sulfation of the corresponding carboxylic acids. Here, the corresponding carboxylic acid and in particular the corresponding fatty acids are reacted with gaseous sulfur trioxide, the sulfur trioxide being used preferably in an amount such that the molar ratio of $SO_3$ to fatty acid is in the range from 1.0:1 to 1.1:1. The crude products obtained in this way, which are acidic sulfation products, are then partially or completely neutralized, preference being given to complete neutralization with aqueous NaOH. If desired, it is also possible to undertake purification steps and/or a bleaching (for adjusting the desired pale color of the products).

In a particularly preferred embodiment, the compounds (A) are used in technical-grade form. This means that the corresponding carboxylic acids, in particular native fatty acid, are sulfated with gaseous sulfur trioxide, as a result of which, following partial or complete neutralization of the resulting acidic sulfation products, a mixture of the compounds (A), (C) and (D) results. By virtue of corresponding adjustments of the reaction parameters (in particular molar ratio of carboxylic acid and sulfur trioxide, and also reaction temperature) it is possible to control the ratio of the compounds (A), (C) and (D). The compounds (C) and (D) are described below in the chapter "Preferred embodiments".

Within the context of the present invention, preference is given to those technical-grade mixtures of the alpha-sulfo fatty acid disalts which have the following composition:
the content of (A) is in the range from 60 to 100% by weight,
the content of (C) is in the range from 0 to 20% by weight,
the content of (D) is in the range from 0 to 20% by weight,
with the proviso that the sum of the components (A), (C) and (D) in this mixture is 100% by weight.

Very particular preference is given to those technical-grade mixtures at have the composition as follows:
the content of (A) is in the range from 70 to 80% by weight,
the content of (C) is in the range from 10 to 15% by weight,
the content of (D) is in the range from 10 to 15% by weight,
with the proviso that the sum of the components (A), (C) and (D) in this mixture is 100% by weight.

The Compounds (B)

The compounds (B), which are referred to in the context of the present invention as amidoalkylbetaines, are obligatory for the aqueous surfactant compositions according to the invention. They have the aforementioned formula (II)

$$R^2-CO-NH-(CH_2)_y-N^+(CH_3)_2-CH_2-COO^- \qquad (II)$$

in which the radical $R^2$ is a linear or branched alkyl or alkenyl radical with 7 to 19 carbon atoms and the index y is an integer in the range 2 to 4. Also applicable—as likewise stated above—is the proviso that the fraction of the compounds (B) in which the radical $R^2$ is an alkenyl radical—based on the total amount of the compounds (B) in the aqueous surfactant compositions—is 3% by weight or less.

The compounds (B) can be prepared by all of the methods known appropriately to the person skilled in the art.

In one embodiment, the index y in the formula (II) is the number 3.

In one embodiment, radical $R^2$ in the formula (II) is a saturated, linear radical with 11 to 17 carbon atoms where, with regard to the compounds (B), it is the case that the fraction of the compounds (B) in which the radical $R^2$ is an undecyl or a tridecyl radical—based on the total amount of the compounds (B)—is 60% by weight or more.

In a preferred composition, the compounds (B) are cocamidopropylbetaine. It is an industrially available product which is typically produced in two steps:

Firstly, coconut fatty acid is reacted with dimethylaminopropylamine (DMAPA, chemical formula $NH_2-(CH_2)_3-N(CH_3)_2$). The resulting amide here is then reacted in a second step with sodium chloroacetate (chemical formula $Cl-CH_2-COONa$) in the presence of NaOH, a quaternization taking place with the elimination of NaCl. The product of technical grade thus obtainable can comprise, besides cocamidopropylbetaine and NaCl, as a consequence of production, as byproducts, glycerol, partial glycerides, glycolic acid, diglycolic acid and free fatty acid, it being possible to reduce the content of these byproducts through the choice of suitable production conditions. If desired, these byproducts can also be further reduced in their content or be eliminated entirely by means of additional purification steps purification.

Preferred Embodiments

In one embodiment, the aqueous surfactant compositions according to the invention comprise, besides the compounds (A), (B) and water, additionally one or more compounds (C) of the general formula (III)

$$R^4COOM^3 \qquad (III)$$

In the formula (III), the radical $R^4$ is a linear or branched alkyl or alkenyl radical with 7 to 19 carbon atoms and the radicals $M^3$ is selected from the group H, Li, Na, K, Ca/2, Mg/2, ammonium and alkanolamines.

In one embodiment, the aqueous surfactant compositions according to the invention comprise, besides the compounds (A), (B) and water, additionally one or more inorganic salts of sulfuric acid (D) of the general formula (IV)

$$(M^4)_2SO_4 \qquad (IV)$$

where $M^4$ is selected from the group Li, Na, K, Ca/2, Mg/2, ammonium and alkanolamine.

The radicals $M^1$ and $M^2$ of the compounds (A), the radical $M^3$ of the compounds (C) and the radical $M^4$ of the compounds (D) can be alkanolamines. In this connection, particular preference is given to monoethanolamine, diethanolamine, triethanolamine and monoisopropanolamine.

In a preferred embodiment, the aqueous surfactant compositions according to the invention comprise the compounds (A), (B), (C) and (D). Here, it is particularly preferred if $M^1$ and $M^2$ of the compounds (A), the radical $M^3$ of the compounds (C) and the radical $M^4$ of the compounds (D) has the meaning Na (sodium).

As explained above, the content of the compounds (A) and (B) in the compositions—based on the total composition—is at least 5% by weight. Preferably, the content of the compounds (A) and (B) in the compositions—based on the total composition—is in the range from 5 to 50% by weight, in particular in the range from 5 to 20% by weight and particularly preferably in the range from 8 to 12% by weight.

In one embodiment, the weight ratio of the compounds (A):(B) in the compositions is in the range from 1:3 to 1:4.

In one embodiment, the pH of the compositions is in the range from 4.3 to 4.7.

The viscosity of the aqueous surfactant compositions—measured using a Brookfield RV laboratory rheometer at 23° C., 12 rpm, spindle set RV 02 to 07 (spindle choice depending on viscosity range)—is preferably 2000 mPas or higher.

If desired, the aqueous surfactant compositions according to the invention can additionally comprise one or more further surfactants which, in structural terms, do not belong to the aforementioned compounds (A), (B), (D) or (E). These surfactants may be anionic, cationic, nonionic or amphoteric surfactants.

Use of the Compositions

A further subject matter of the invention is the use of the aforementioned compositions for cosmetic products, and also detergents and cleaners.

With regard to cosmetic products, particular preference is given here especially to those which are present in the form of hair shampoos, shower gels, soaps, syndets, washing pastes, washing lotions, scrub preparations, foam baths, oil baths, shower baths, shaving foams, shaving lotions, shaving creams and dental care products (for example toothpastes, mouthwashes and the like).

With regard to cleaners, of preference here are in particular products with a low pH for cleaning hard surfaces, such as bath and toilet cleaners and the like, and also for cleaning and/or scented gels for use in sanitary installations.

EXAMPLES

Substances Used

Demin. Water=Demineralized Water

SFA-I: alpha-sulfo fatty acid disalt of technical grade based on native $C_{12/14}$-fatty acid; composition: 74% by weight disodium 2-sulfolaurate, 13% by weight sodium laurate, 11% by weight sodium sulfate, 2% by weight water. The term "laurate" here means that the $C_{12/14}$ weight ratio of the mixture of the underlying native fatty acids is 70:30.

SFA-II: purified alpha-sulfo fatty acid disalt based on native $C_{12/14}$-fatty acid; composition: 90% by weight disodium 2-sulfolaurate, 5% by weight sodium laurate, 0.2% by weight sodium sulfate, 4.8% by weight water. The term "laurate" here means that the $C_{12/14}$ weight ratio of the mixture of the underlying native fatty acids is 70:30.

Dehyton PK 45: Cocamidopropylbetaine, 37% active substance (BASF PCN)

Measurement and Test Methods pH: Using a standard commercial pH meter, the pH was measured directly in the formulation, i.e. the aqueous surfactant composition.

Viscosity: The viscosities of the aqueous surfactant compositions was measured using a Brookfield RV laboratory rheometer at 23° C., 12 rpm, spindle set RV 02 to 07 (spindle selection according to viscosity range).

Note: Viscosity data labeled with (*) are almost cut-resistant gels which can actually no longer be measured using the Brookfield rheometer since the spindles slip through and cut through the gel. The values stated here with the addition (*) were therefore ascertained at very low rotational speed (0.6 rpm); although they are merely approximate reference values they do have some informative value.

Homogeneity and appearance: Assessment of the homogeneity and appearance of the aqueous surfactant compositions was carried out visually (with the naked eye) in a 125 ml wide-neck glass bottle. The homogeneity was assessed first here. In the context of the present invention, homogeneity is understood as meaning that no creaming visible to the naked eye or a sediment arises. If the compositions were assessed as homogeneous, their appearance was also assessed and characterized for example with attributes such as slightly opaque (but always still clearly translucent) to water-clear.

Transparency: The quantitative determination of the transparency of a number of aqueous surfactant compositions was carried out using a TurbiScan MA 2000 (Formulaction). Here, firstly 5 ml samples of the aqueous surfactant compositions to be tested were placed into the instrument-specific measuring cell and left to stand for 24 hours at room temperature (23° C.) until all of the air bubbles had escaped. Then, the transmission of the incident light (wave-length 850 nm) was measured over a sample level from 20 mm to 50 mm. The evaluation was carried out using the Turbisoft software (Version 1.2.1.) supplied by the manufacturer of the measuring instrument: For each measurement, an average value of the transmission (in %) above the sample level is output by the software. This average value is called average transmission for the purposes of the present application. Here, the transmission measurement was repeated 3 times for each sample and the numerical average value was formed from the resulting values for the average transmission. This value is given in table 1 in the column "transparency" (numerical average of the experimental data of the average transmission from three measurements).

Where no transmission value is given in the tables, the assessment was made exclusively with the naked eye in a 125 ml wide-neck glass bottle.

Foam test: The aqueous surfactant compositions were diluted with tap water (about 13.8° German hardness, adjusted to pH 4.5-4.6 with HCl) in the weight ratio 1:9 and heated to 30° C. 100 g of the aqueous solutions prepared in this way were foamed using a Meiser disk in a cylindrical 800 ml beaker with a low shape (diameter 10.5 cm) at 2000 revolutions/min for 10 s. The foam height in centimeters (cm) was read off. A triple determination was carried out. The result given was the average value with standard deviation.

Shelf Life:

The surfactant compositions were stored at 23° C. for a period of 8 weeks. Then, the testing of the two parameters homogeneity and appearance of the compositions was carried out. The compositions were then considered to be storage-stable if both parameters remained unchanged over the entire period of 8 weeks.

EXAMPLES

Example 1: High-Viscosity, Transparent Gel Formulation (Preparation Example)

Preparation (batch size 200 g): 8.1 g of SFA-I and 48.6 g of Dehyton PK 45 were dissolved with stirring at 23° C. in 143.2 g of demin. water (cf. table 1). Then, the pH was adjusted to 4.7 by adding citric acid (50% strength solution).

The assessed parameters (viscosity, homogeneity, appearance, foam, shelf life, transparency) can be found in table 1.

Example 1 shows that very high viscosities can be achieved with this surfactant system without adding thickeners.

In the foam test, this formulation according to example 1 exhibited a foam level of 7.6 cm+/−0.23 cm and thus foamed significantly more than the respective individual surfactants (compare comparative examples 1 and 2).

Over and above the assessment of the two aforementioned parameters homogeneity and appearance, that are decisive for the shelf life, the following test was additionally carried out: The surfactant composition were cooled in the freezer at a temperature of −8° C. to the point of complete solidification. The samples were then allowed to thaw again at a temperature of 23° C. The homogeneity and the appearance of the thawed samples were then assessed; both parameters were unchanged, i.e. the samples were homogeneous and clear.

Example 2: Transparent Formulation with Shower Gel Viscosity (Application Example)

Preparation as example 1, but with changed amounts of the components used (see table 1). pH adjustment as in table 1 with citric acid (to the value given in table 1). The assessed parameters (viscosity, homogeneity, appearance, shelf life, transparency) can be found in table 1.

The viscosity of the formulation according to example 2 was significantly lower than in example 1. The value of 4100 mPas would be suitable for example for a shower gel.

Example 3: High-Viscosity, Transparent Gel Formulation with a Lower Active Substance Content (Application Example)

Preparation as example 1, but with changed amounts of the components used (see table 1). pH adjustment as in example 1 with citric acid (to the value stated in table 1). The assessed (viscosity, homogeneity, appearance, shelf life, transparency) can be found in table 1.

Example 3 shows that the thickening effect is also still present in the case of a reduced active substance content (here only 8% by weight).

TABLE 1

|  | Example 1 | Example 2 | Example 3 |
|---|---|---|---|
| SFA-I | 8.1 g | 5.4 g | 5.4 g |
| Dehyton PK 45 | 48.6 g | 54.1 g | 32.4 g |
| Demin. water | 143.3 g | 140.5 g | 162.2 g |
| pH | 4.7 | 4.5 | 4.7 |
| Viscosity | Gel >230000 mPas(*) | 4100 mPas | Gel >180000 mPas(*) |
| Homogeneity | homogeneous | homogeneous | homogeneous |
| Appearance | clear | clear | slightly opaque |
| Foam test | 7.6 cm |  |  |
| Shelf life | storage-stable | storage-stable | storage-stable |
| Transparency | 92.9% | 92.3% | 89.7% |
| Active substance content | 12% | 12% | 8% |
| Ratio (A):(B) (% by weight of active substance) | 1:3 | 1:5 | 1:3 |

Note:
In table 1 and also in tables 2 and 3, active substance is understood as meaning the sum of the anionic surfactants and the amphoteric surfactants. The data are in % by weight.

Example 4: Viscous, Transparent Gel Formulation

Preparation as example 1, but with changed amounts of the components used and also use of SFA-II instead of SFA-I (see table 2). pH adjustment as in example 1 with citric acid (to the value of 4.7 given in table 2). The assessed parameters (viscosity, homogeneity, appearance, shelf life) can be found in table 2.

TABLE 2

|  | Example 4 |
|---|---|
| SFA-II | 6.7 g |
| Dehyton PK 45 | 48.6 g |
| Dehyton AB 30 |  |
| Texapon NSO |  |
| Demin. water | 144.7 g |
| pH | 4.7 |
| Viscosity | gel >30000 mPas(*) |
| Homogeneity | homogeneous |
| Appearance | clear |
| Shelf life | storage-stable |
| Active substance content | 12% |
| Ratio (A):(B) (% by weight of active substance) | 1:3 |

Comparative Example 1: Formulation Comprising Exclusively SFA-I

Preparation as example 1, but with changed amounts of the components used (see table 3). pH adjustment as in example 1 with citric acid (to the value given in table 3). The assessed parameters (viscosity, homogeneity, appearance, foam) can be found in table 3.

The present comparative example shows that a formulation which comprises exclusively SFA-I does not achieve essential aims of the objective. Neither could the anionic surfactant SFA-I be dissolved in water, nor was a thickening effect evident. In the foam test, this formulation achieved merely a foam level of 5.1 cm+/−0.36 cm, which is significantly worse than the foam level measured in example 1.

Comparative Example 2: Formulation Comprising Exclusively Dehyton PK 45

Preparation as example 1, but with changed amounts of the components used (see table 3). pH adjustment as in example 1 with citric acid (to the value given in table 3). The assessed parameters (viscosity, homogeneity, appearance, foam) can be found in table 3.

The present comparative example shows that a formulation which comprises exclusively Dehyton PK 45 does not achieve essential aims of the objective. Neither was a thickening effect achieved, nor did this formulation achieve an acceptable value in the foam test. The measured foam level was 5.5 cm+/−0 cm, which is significantly worse than the foam level measured in example 1.

TABLE 3

|  | Comparative example 1 | Comparative example 2 | Comparative example 3 |
|---|---|---|---|
| SFA-I | 32.4 g |  | 8.1 g |
| Dehyton PK 45 |  | 64.9 g | 48.6 g |
| Dehyton AB 30 |  |  |  |
| Texapon NSO |  |  |  |
| Demin. water | 167.6 g | 135.1 g | 143.3 g |
| pH | 4.5 | 4.5 | 6.0 |
| Viscosity | immeasurably low, supernatant phase water-thin | 100 mPas | 100 mPas |
| Homogeneity | not homogeneous | homogeneous | not homogeneous |
| Appearance | milky cloudy dispersion; separated after some time into clear supernatant phase and white sediment | clear | cloudy dispersion; separated after some time and formed sediment |
| Active substance content | 12% | 12% | 12% |
| Foam test | 5.1 cm | 5.5 cm |  |
| Ratio (A):(B) (% by weight of active substance) | 1:0 | 0:1 | 1:3 |

Comparative Example 3: Formulation with pH not According to the Invention

Preparation as example 1, but with changed amounts of the components used (see table 3). pH adjustment as in example 1 with citric acid (to the value of 6.0 given in table 3). The assessed parameters (viscosity, homogeneity, appearance) can be found in table 3.

The present comparative example shows that a formulation whose pH is not according to the invention does not achieve significant aims of the objective. Neither was a clear solution produced, nor was a thickening effect achieved. This demonstrates that the pH is a critical parameter, i.e. is essential to the invention, for this.

The invention claimed is:

1. An aqueous surfactant composition comprising:
  (a) two or more alpha-sulfo fatty acid disalt (A) of general formula (I), $$R^1CH(SO_3M^1)COOM^2 \qquad (I),$$

in which (i) radical $R^1$ is a saturated, linear alkyl radical with 10 to 16 carbon atoms, at least some of $R^1$ is a decyl radical, at least some of $R^1$ is a dodecyl radical, and the fraction of the compound (A) in which the radical $R^1$ is the decyl or the dodecyl radical based on the total amount of the compound (A) is 90% by weight or more, and (ii) radicals $M^1$ and $M^2$, independently of one another, are selected from the group consisting of H, Li, Na, K, Ca/2, Mg/2, ammonium, and alkanolamine,
  (b) one or more amidoalkylbetaine (B) of general formula (II), $$R^2\text{—CO—NH—}(CH_2)_y\text{—N}^+(CH_3)_2\text{—CH}_2\text{—COO}^- \qquad (II),$$

in which radical $R^2$ is a linear or branched alkyl or alkenyl radical with 7 to 19 carbon atoms and the index y is an integer in the range 2 to 4,
  (c) one or more compound (C) of general formula (III), $$R^4COOM^3 \qquad (III),$$

in which the radical $R^4$ is a linear or branched alkyl or alkenyl radical with 7 to 19 carbon atoms and the radical $M^3$ is selected from the group consisting of H, Li, Na, K, Ca/2, Mg/2, ammonium, and alkanolamine,
  (d) one or more inorganic salt of sulfuric acid (D) of general formula (IV), $$(M^4)_2SO_4 \qquad (IV),$$

wherein $M^4$ is selected from the group consisting of Li, Na, K, Ca/2, Mg/2, ammonium, and alkanolamine, and
  (e) water,
  where the following provisos apply:
    the aqueous surfactant composition is free from one or more ester sulfonate (E) of the general formula (V), $$R^5CH(SO_3M^5)COOR^6 \qquad (V),$$

in which radical $R^5$ is a linear or branched alkyl or alkenyl radical with 6 to 18 carbon atoms and radical $R^6$ is a linear or branched alkyl or alkenyl radical with 1 to 20 carbon atoms, and the radical $M^5$ is selected from the group consisting of Li, Na, K, Ca/2, Mg/2, ammonium, and alkanolamines;
    the aqueous surfactant composition is free from additional surfactants having an alkoxy group other than components (A)-(D);
    with regard to the compound (B), it is the case that the fraction of the compound (B) in which the radical $R^2$ is an alkenyl radical, based on the total amount of the compound (B) in the aqueous surfactant composition, is 3% by weight or less;
    the content of the compounds (A) and (B) in the aqueous surfactant composition is, based on the total aqueous surfactant composition, at least 5% by weight;
    a weight ratio of the compounds (A):(B) in the aqueous surfactant composition is in the range from 1:1.5 to 1:5;
    the content of (A) is in the range from 60 to 100% by weight based on the sum of compounds (A), (C), and (D) in the aqueous surfactant composition;
    the content of (C) is in the range from more than 0 to 20% by weight based on the sum of compounds (A), (C), and (D) in the aqueous surfactant composition;
    the content of (D) is in the range from more than 0 to 20% by weight based on the sum of compounds (A), (C), and (D) in the aqueous surfactant composition;
    a pH of the aqueous surfactant composition is 5.8 or less;
    a viscosity of the aqueous surfactant composition, measured using a Brookfield RV laboratory rheometer at 23° C., 12 rpm, spindle set RV 02 to 07 (spindle choice depending on viscosity range), is 1000 mPas or higher; and
    an average transmission of the aqueous surfactant composition at 23° C., measured using a TurbiScan MA 2000, is at least 80%.

2. The composition according to claim 1, wherein the index y in the formula (II) is the number 3.

3. The composition according to claim 1, wherein the radical $R^2$ in the formula (II) is a saturated, linear radical with 11 to 17 carbon atoms, where, with regard to the compound (B), it is the case that the fraction of the compound (B) in which the radical $R^2$ is an undecyl or a tridecyl radical, based on the total amount of the compound (B), is 60% by weight or more.

4. The composition according to claim 1, where the compound (B) comprises cocamidopropylbetaine.

5. The composition according to claim 1, where the radicals $M^1$ and $M^2$ are Na.

6. The composition according to claim 1, wherein a content of the compounds (A) and (B) in the composition, based on the total composition, is in a range from 8 to 12% by weight.

7. The composition according to claim 1, wherein a weight ratio of the compounds (A):(B) in the composition is in a range from 1:3 to 1:4.

8. The composition according to claim 1, wherein the pH of the composition is in a range from 4.3 to 4.7.

9. The composition according to claim 1, wherein the viscosity of the composition, measured using a Brookfield RV laboratory rheometer at 23° C., 12 rpm, spindle set RV 02 to 07 (spindle choice depending on viscosity range), is 2000 mPas or higher.

10. A cosmetic product, detergent, or cleaner comprising a composition according to claim 1.

11. A cosmetic product comprising a composition according to claim 1, the cosmetic product in the form of hair shampoos, shower gels, soaps, syndets, washing pastes, washing lotions, scrub preparations, foam baths, oil baths, shower baths, shaving foams, shaving lotions, shaving creams, or dental care products.

12. A product for cleaning hard surfaces comprising a composition according to claim 1, said product having a pH of 5.8 or less.

13. The product of claim 12 in the form of bath cleaners, toilet cleaners, and cleaners and/or fragrance gels for sanitary installations.

14. The composition according to claim 1, wherein radical $R^6$ is an alkenyl radical or is branched above 3 carbon atoms.

15. The composition according to claim 1, wherein:
the content of (A) is in the range from 70 to 80% by weight based on the sum of components (A), (C), and (D) in the aqueous surfactant composition;
the content of (C) is in the range from 10 to 15% by weight based on the sum of components (A), (C), and (D) in the aqueous surfactant composition; and
the content of (D) is in the range from 10 to 15% by weight based on the sum of components (A), (C), and (D) in the aqueous surfactant composition.

16. The composition according to claim 1, wherein the aqueous surfactant composition is free from alkylbetaines.

17. An aqueous surfactant composition comprising:
(a) two or more alpha-sulfo fatty acid disalt (A) of general formula (I), $$R^1CH(SO_3M^1)COOM^2 \qquad (I),$$

in which (i) radical $R^1$ is a saturated, linear alkyl radical with 10 to 16 carbon atoms, at least some of $R^1$ is a decyl radical, at least some of $R^1$ is a dodecyl radical, and the fraction of the compound (A) in which the radical $R^1$ is the decyl or the dodecyl radical based on the total amount of the compound (A) is 90% by weight or more, and (ii) radicals $M^1$ and $M^2$, independently of one another, are selected from the group consisting of H, Li, Na, K, Ca/2, Mg/2, ammonium, and alkanolamine, (b) one or more amidoalkylbetaine (B) of general formula (II), $$R^2\text{—CO—NH—}(CH_2)_y\text{—N}^+(CH_3)_2\text{—CH}_2\text{—COO}^- \qquad (II),$$

in which radical $R^2$ is a linear or branched alkyl or alkenyl radical with 7 to 19 carbon atoms and the index y is an integer in the range 2 to 4, (c) one or more compound (C) of general formula (III), $$R^4COOM^3 \qquad (III),$$

in which the radical $R^4$ is a linear or branched alkyl or alkenyl radical with 7 to 19 carbon atoms and the radical $M^3$ is selected from the group consisting of H, Li, Na, K, Ca/2, Mg/2, ammonium, and alkanolamine, (d) one or more inorganic salt of sulfuric acid (D) of general formula (IV), $$(M^4)_2SO_4 \qquad (IV),$$

wherein $M^4$ is selected from the group consisting of Li, Na, K, Ca/2, Mg/2, ammonium, and alkanolamine, and (e) water, where the following provisos apply:
the aqueous surfactant composition is free from one or more ester sulfonate (E) of the general formula (V), $$R^5CH(SO_3M^5)COOR^6 \qquad (V),$$

in which radical $R^5$ is a linear or branched alkyl or alkenyl radical with 6 to 18 carbon atoms and radical $R^6$ is a linear or branched alkyl or alkenyl radical with 1 to 20 carbon atoms, and the radical $M^5$ is selected from the group consisting of Li, Na, K, Ca/2, Mg/2, ammonium, and alkanolamines;

the aqueous surfactant composition is free from anionic surfactants other than components (A)-(D);

with regard to the compound (B), it is the case that the fraction of the compound (B) in which the radical $R^2$ is an alkenyl radical, based on the total amount of the compound (B) in the aqueous surfactant composition, is 3% by weight or less;

the content of the compounds (A) and (B) in the aqueous surfactant composition is, based on the total aqueous surfactant composition, at least 5% by weight;

a weight ratio of the compounds (A):(B) in the aqueous surfactant composition is in the range from 1:1.5 to 1:5;

the content of (A) is in the range from 60 to 100% by weight based on the sum of compounds (A), (C), and (D) in the aqueous surfactant composition;

the content of (C) is in the range from more than 0 to 20% by weight based on the sum of compounds (A), (C), and (D) in the aqueous surfactant composition;

the content of (D) is in the range from more than 0 to 20% by weight based on the sum of compounds (A), (C), and (D) in the aqueous surfactant composition;

a pH of the aqueous surfactant composition is 5.8 or less;

a viscosity of the aqueous surfactant composition, measured using a Brookfield RV laboratory rheometer at 23° C., 12 rpm, spindle set RV 02 to 07 (spindle choice depending on viscosity range), is 1000 mPas or higher; and an average transmission of the aqueous surfactant composition at 23° C., measured using a TurbiScan MA 2000, is at least 80%.

* * * * *